United States Patent
Platte et al.

(10) Patent No.: US 9,423,367 B2
(45) Date of Patent: Aug. 23, 2016

(54) PERMEABLE MEASURING CELL FOR RECEIVING MEASURING MEANS

(75) Inventors: Daniel Platte, Velbert (DE); Peter Schroeren, Kempen (DE); Jürgen Danulat, Mettmann (DE); Andreas Reese, Essen (DE)

(73) Assignee: Optek-Danulat GmbH, Essen (DE)

( * ) Notice: Subject to any disclaimer, the term of this patent is extended or adjusted under 35 U.S.C. 154(b) by 189 days.

(21) Appl. No.: 14/002,808

(22) PCT Filed: Feb. 27, 2012

(86) PCT No.: PCT/EP2012/053254
§ 371 (c)(1),
(2), (4) Date: Sep. 3, 2013

(87) PCT Pub. No.: WO2012/119876
PCT Pub. Date: Sep. 13, 2012

(65) Prior Publication Data
US 2014/0004002 A1    Jan. 2, 2014

(30) Foreign Application Priority Data
Mar. 4, 2011   (DE) .................. 10 2011 013 001

(51) Int. Cl.
| G01N 21/00 | (2006.01) |
| G01N 27/04 | (2006.01) |
| G01N 21/05 | (2006.01) |
| G01N 23/00 | (2006.01) |
| A61L 2/08 | (2006.01) |

(52) U.S. Cl.
CPC .............. *G01N 27/04* (2013.01); *G01N 21/05* (2013.01); *G01N 23/00* (2013.01); *A61L 2/081* (2013.01); *A61L 2202/14* (2013.01); *G01N 2021/054* (2013.01)

(58) Field of Classification Search
None
See application file for complete search history.

(56) References Cited

U.S. PATENT DOCUMENTS 5,864,140 A * 1/1999 Owens .......................... 250/343
5,923,433 A * 7/1999 Giuffre et al. ................. 356/440

(Continued)

FOREIGN PATENT DOCUMENTS

| DE | 9315488 | 2/1994 | ............ G01D 11/30 |
| DE | 19532382 | 3/1997 | ............ G01N 21/03 |

(Continued)

OTHER PUBLICATIONS

Int'l Search Report from corresponding PCT/EP2012/053254 (Form PCT/ISA/210); 2 pages.

*Primary Examiner* — Jill Warden
*Assistant Examiner* — Brittany Fisher
(74) *Attorney, Agent, or Firm* — Kusner & Jaffe

(57) ABSTRACT

A flow-through measuring cell for accommodating measuring means for measuring chemical and/or physical properties of a fluid which is flowing through the measuring cell, the measuring cell having an inlet opening for entry of the fluid, an outlet opening for exit of the fluid, a, especially single, measuring space which is located between the inlet opening and outlet opening, a radiation measurement region for measuring the interaction of the fluid in the measuring cell with electromagnetic radiation from outside the measuring cell, a conductivity measurement receiver for accommodating conductivity measuring means for measuring the conductivity of the fluid in the measuring cell and/or a pH measurement receiver for accommodating the pH value measuring means for measuring the pH value of the fluid in the measuring cell.

3 Claims, 3 Drawing Sheets

(56) References Cited

U.S. PATENT DOCUMENTS

| | | | | |
|---|---|---|---|---|
| 2003/0203270 | A1* | 10/2003 | Rock | H01M 8/2475 429/470 |
| 2007/0091304 | A1* | 4/2007 | Mueller | G01N 21/05 356/246 |
| 2007/0097361 | A1* | 5/2007 | Beigel | B01L 3/561 356/246 |
| 2009/0134882 | A1* | 5/2009 | Schick et al. | 324/601 |
| 2010/0269940 | A1* | 10/2010 | Wynn et al. | 138/90 |
| 2010/0317093 | A1* | 12/2010 | Turewicz et al. | 435/287.2 |

FOREIGN PATENT DOCUMENTS

| | | | |
|---|---|---|---|
| EP | 0 089 157 | 9/1983 | G01N 21/05 |
| EP | 1 921 439 | 5/2008 | G01N 21/03 |
| GB | 2 282 880 | 4/1995 | G01N 21/05 |
| GB | 2 446 934 | 8/2008 | G01N 21/01 |

\* cited by examiner

PERMEABLE MEASURING CELL FOR RECEIVING MEASURING MEANS

FIELD OF THE INVENTION

This invention relates to a flow-through measuring cell for accommodating measuring means for measuring chemical and/or physical properties of a fluid which is flowing through the measuring cell.

BACKGROUND OF THE INVENTION

Flow-through measuring cells for control and validation, as well as adherence to certain stipulations, are now indispensable especially in biotechnology and food technology. Application examples are chromatography or ultrafiltration.

The accuracy of the measuring cells during the measurement and the rapid response are especially important. For these reasons, measuring cells to date have been produced from very high quality materials, for example high-grade steel. One important aspect is also the possibility of cleaning, especially since measuring cells are often used inline.

Since, especially in biotechnology, very expensive fluids are often studied, the volume of the measuring cell and corresponding dead spaces play a major part. Thus, there is the effort to reduce the volume of the measuring space of the measuring cells as much as possible in order for example to keep carryover during a phase change and corresponding material consumption of expensive media as small as possible.

But the draining property of the measuring cell is also decisive so that after the end of the measurement process no residues of the fluid remain in the measuring space any longer.

Not only does cleaning, but also the possibility of sterilization plays a decisive part.

SUMMARY OF THE INVENTION

The object of this invention is therefore to devise a flow-through measuring cell which has been optimized according to the aforementioned stipulations.

Advantageous developments of the invention are given in the dependent claims. All combinations of at least two of the features given in the specification, the claims and/or the figures also fall within the scope of the invention. At the given value ranges, values within the indicated limits will also be considered to be disclosed as boundary values and will be claimed in any combination.

The invention is based on the idea of devising a measuring cell wherein at a volume of the measuring space as small as possible both a measurement with electromagnetic radiation and also a conductivity measurement and/or a pH measurement and/or a temperature measurement can be taken. Thus, at least two measurements in one measuring space are enabled by the configuration of a flow-through measuring cell according to the present invention, of which one measurement is a radiation measurement with electromagnetic radiation. In particular for the radiation measurement, to determine the interaction of the fluid with the electromagnetic radiation a certain beam path is necessary so that a reduction of the volume is hardly possible. The invention therefore provides at least one other measurement in the same measuring space in order to reduce the volume which has been necessary to date for the two measurements altogether and the number of the measuring cells to be installed.

According to one advantageous embodiment of the invention, it is provided that the measuring cell comprises at least predominantly, especially to at least 90%, preferably to at least 95%, of chemical elements with an atomic number <17. Thus, the measuring cell is gamma-permeable to such an extent that complete and homogeneous exposure of the measuring space to gamma rays for disinfection is enabled. In this way, the production and shipping or transport of the measuring cells according to the present invention are greatly simplified since the measuring cells in the packaged state can be exposed to gamma rays and can be disinfected accordingly. Thus contamination in the packaging of the measuring cells can be precluded and the packaging can be carried out accordingly more economically.

By the measuring cell having a temperature measurement range for placement, especially for connection, of a temperature sensor, a temperature measurement can be easily integrated into the measuring cell in addition.

According to one advantageous embodiment of the invention, the invention proceeds in a direction opposite the prior art by the measuring cell being made as a disposable measuring cell, especially predominantly, preferably essentially completely of plastic. In this way, it is possible to replace the high-quality and expensive measuring means which is necessary for the measurement and to which especially high quality requirements apply after each cycle or after a certain time interval or even with each changing of a fluid while the expensive measuring means can continue to be used.

In this invention it is especially advantageous that according to one embodiment of the invention, the predominantly tubular measuring space has a volume of less than 50 ml, especially less than 30 ml. Thus a plurality of measurements on the fluid which is flowing through the measuring cell are enabled on an extremely small space and the material consumption and the carryover during phase changing are minimized.

By the inlet opening and the outlet opening running in parallel offset to one another, the measuring cell can be optimally installed in existing systems. This moreover facilitates the mounting of the measuring cell.

An especially good flow profile with optimum drainage behavior can be implemented by the measuring cell being configured such that the fluid runs from the inlet opening to the outlet opening at least through one, especially two, preferably exactly two bends. The bends have especially a bending angle of at least 45°, preferably roughly 90°. In this way, on the measuring cell several free surfaces for attachment of measuring means are formed.

According to another advantageous embodiment of the invention, it is provided that a beam path of the radiation measurement region runs transversely to the measuring space and transversely to the inlet opening and/or the outlet opening. In this way the radiation measurement is implemented with the smallest possible space requirement in or on the measuring cell.

For the conductivity measurement receiver and/or the pH measurement receiver, according to another advantageous embodiment of the invention, it holds that it is or they are located lengthwise to the measuring space and transversely to the inlet opening and/or the outlet opening. In this way, with optimum space utilization a complete integration of the indicated measuring means can be achieved with the smallest possible volumes.

The system as claimed in the invention is optimized by the measuring cell being used or usable as a disposable measuring cell for one measurement cycle according to one advantageous embodiment, while the radiation measuring means and/or the conductivity measuring means and/or the pH value measuring means are used or usable for several measurement cycles.

Other advantages, features and details of the invention will become apparent from the following description of preferred exemplary embodiments and using the drawings.

DETAILED DESCRIPTION OF PREFERRED EMBODIMENTS

In the figures the same elements and elements with the same action or elements with the same function are identified with the same reference numbers.

Figure 1:
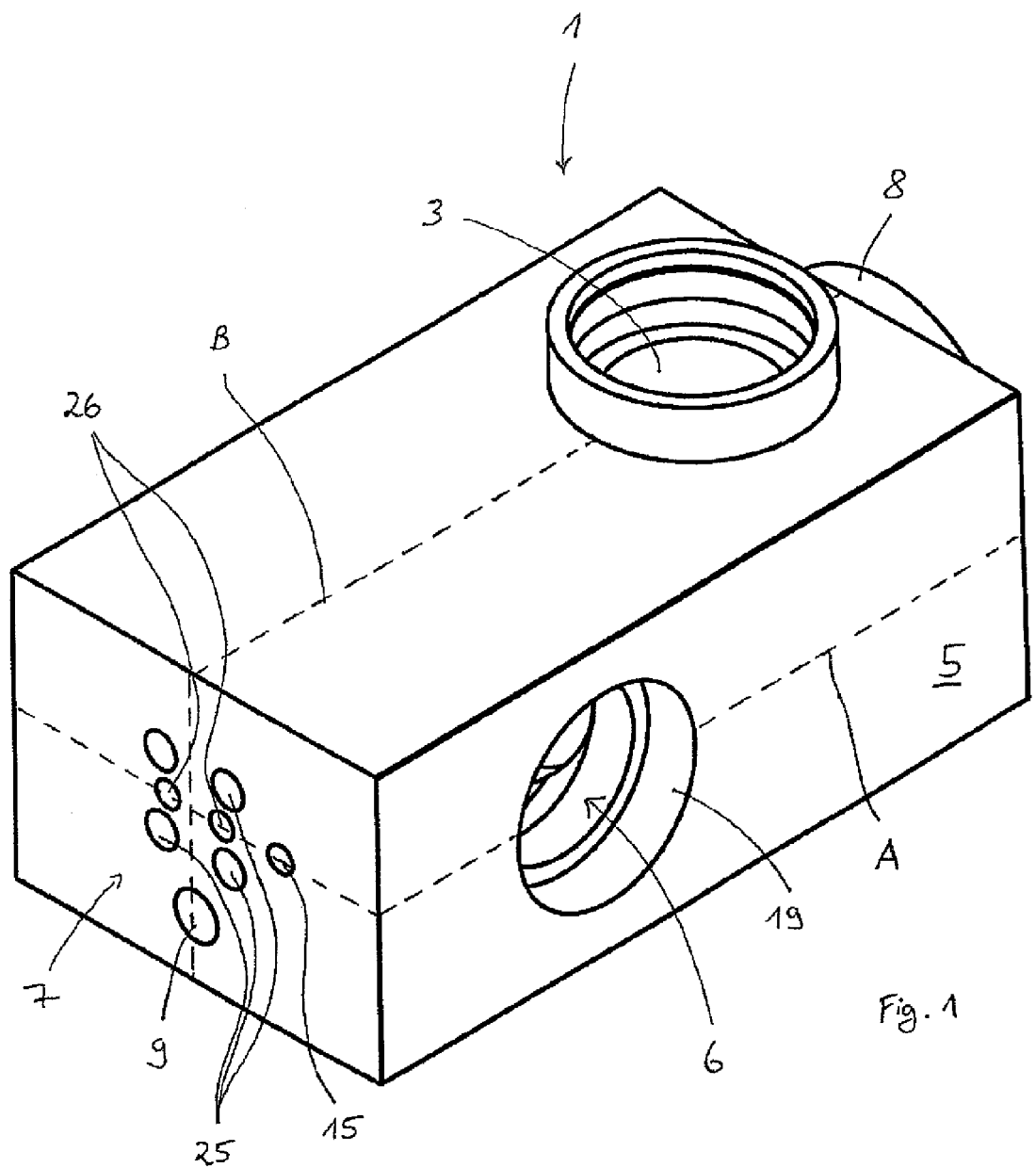
FIG. 1 shows a perspective view of a measuring cell as claimed in the invention with cutting plane A and cutting plane B.
Figure 2:
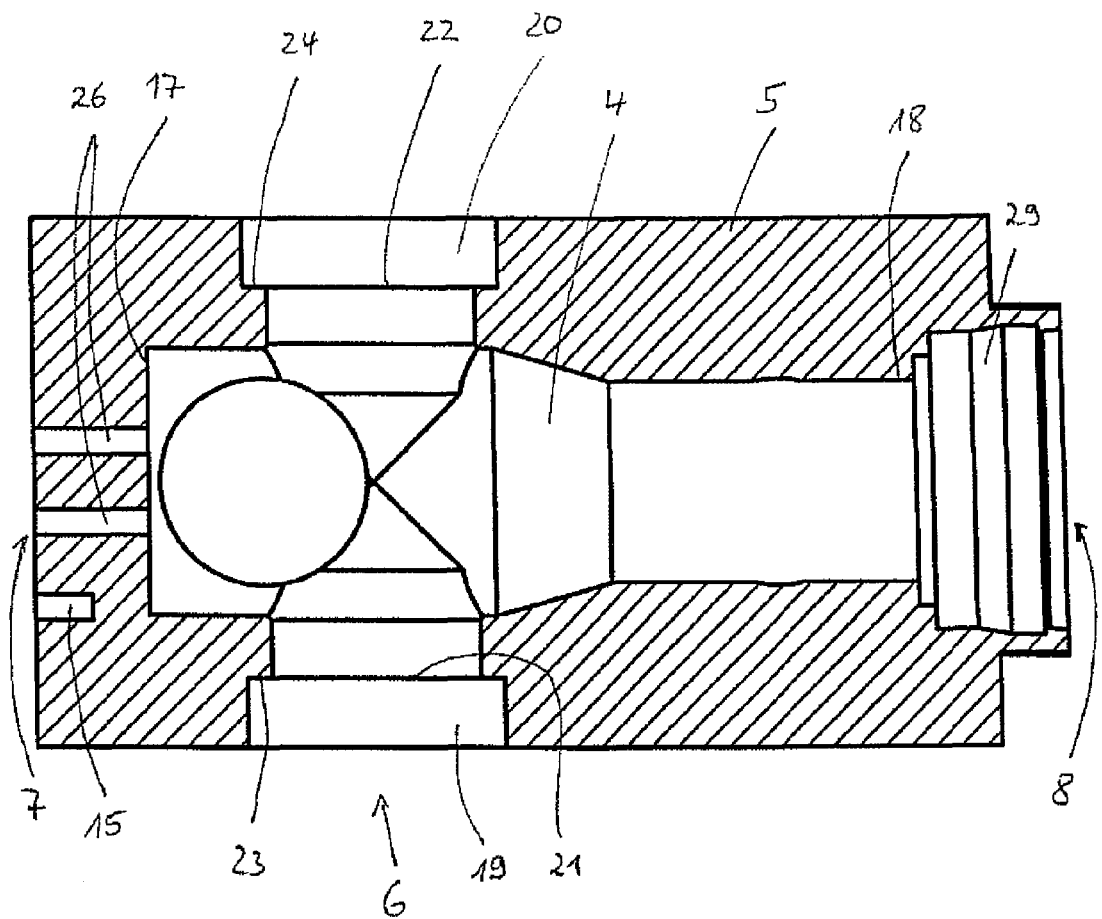
FIG. 2 shows a cutaway view of a measuring cell according to cutting plane A from FIG. 1.

FIG. 1 shows an essentially cuboidal flow-through measuring cell 1 with diverse means which are described below for accommodating measuring means for measuring chemical and/or physical properties of a fluid which is flowing through the measuring cell 1.

Figure 3:
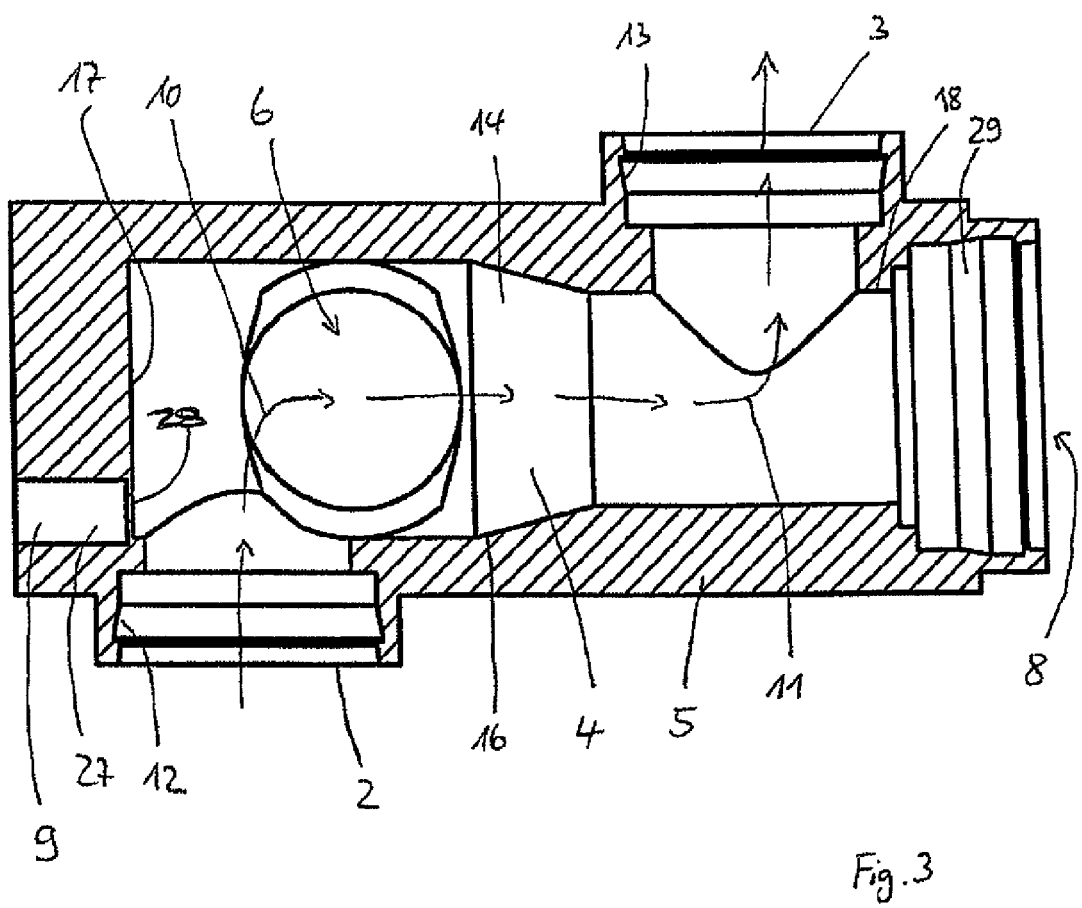
FIG. 3 shows a cutaway view of a measuring cell according to cutting plane B from FIG. 1.

FIG. 3 shows, using schematic arrows (flow path), that the fluid travels through an inlet opening 2 for entry of the fluid into a measuring space 4. The measuring space 4 extends at an angle of 90° to the inlet opening 2 to the right so that the fluid follows a bend 10 and thus a curve which is shown schematically by an arrow. After the fluid has flowed through the measuring space 4, the fluid emerges from the measuring cell 1 through an outlet opening 3. Shortly in front of the outlet opening 3 there is a bend 11 which runs in the opposite direction of the bend 10 so that the fluid in turn follows a curve which is shown by an arrow by 90°.

Both on the inlet opening 2 and also on the outlet opening 3 there are connecting means 12, 13 via which the measuring cell 1 can be connected to corresponding connections into the course of the process as an inline measuring cell. In the middle region of the measuring space 4 there is an especially conical reduction 14 of the measuring space 4 in order to ensure fluid flow which is laminar or as free of bubbles as possible. On the connection means 12, 13 there are sealing means. For the connection means 12, 13 there are advantageously adapters made especially as disposable adapters for especially pluggable connection of various line connections. The adapters are formed especially from plastic and are packaged at the same time with the measuring cell and are made available as a measuring cell set. This measuring cell set offers the advantage that inline installation can take place without problems, quickly and reliably onto different line systems and thus the warehousing costs are also reduced.

The measuring cell 1 is comprised essentially of a one-piece measuring cell body 5 of plastic, especially polyphenolene sulfone. Properties of the plastic as claimed in the invention include: precise workability, high stiffness, gamma permeability and high combustibility, i.e. up to at least 95% of the mass can be converted into the gaseous phase in processes of garbage incineration which are conventional at present.

By providing coding 15, the measuring cell 1 can be coupled especially automatically to the measuring means with avoidance of a twisted or incorrect connection. For this purpose there are corresponding coupling means on the line to be connected or on a receiver for the measuring cell 1 on the line.

The coding 15 or additional coding in one advantageous embodiment of the invention encompasses parameter recognition for one or more parameters of the measuring cell 1. The parameter recognition can be comprised of a geometrical execution of the coding 15 or the additional coding which are detected by the coupling means or separate detection means. Mechanical or electronic parameter recognition is especially advantageous. Especially a transponder for identification using electromagnetic waves is possible as electronic parameter recognition.

The parameters are especially the cell constant for the measurement of conductivity and/or the optical path length of the respective measuring cell 1.

The measuring space 4 has an especially tubular (preferably with a circular cross section) measuring channel 16 which extends more or less over the entire length of the measuring cell 1. On a first end 17 of the measuring channel 16 the inlet opening 2 on the measuring channel 16 is located angled, while on a second end 18 of the measuring channel 16 the outlet opening 3 is located angled, in the opposite direction to the inlet opening 2.

The axial direction of the inlet opening 2 and the axial direction of the outlet opening 3 are parallel to one another and run transversely or at an angle of 90° to the axial direction of the measuring channel 16.

Transversely or at an angle of 90° to the measuring channel and especially also transversely or at an angle of 90° to the axial direction of the inlet opening 2 or of the outlet opening 3 there is a radiation measurement region 6 for measurement of the interaction of the fluid in the measuring cell 1 with electromagnetic radiation. Electromagnetic radiation from a radiation source which is not shown enters the measuring space 4 through a radiation inlet opening 19 and emerges again from the measuring space 4 on the opposite side through a radiation outlet opening 20, where it is incident on a radiation measurement apparatus. The beam path runs transversely or at an angle of 90° to the measuring channel 16 and the inlet opening 2 or the outlet opening 3. The axial direction of the radiation inlet opening 19 and radiation outlet opening 20 which are flush with one another coincides with the beam path.

In the radiation inlet opening 19 and in the radiation outlet opening 20 there are window receivers 21, 22 for accommodating the windows which are transparent to the electromagnetic radiation of the radiation source. The windows seal the measuring space 4 relative to the environment.

The measuring space 4 is made as claimed in the invention such that in the beam path at least between the radiation inlet opening 19 and the radiation outlet opening 20, especially between the windows, there are no other components which can disturb the measurement.

The optical path length, therefore the distance which the electromagnetic radiation traverses in passage through the fluid, is formed by the windows' adjoining the stops 23, 24 of the window receivers 21, 22.

On the first end 17 there is a conductivity measurement receiver 7 for accommodating the conductivity measuring means for measuring the conductivity of the fluid in the measuring cell 1. The conductivity measurement receiver 7 in this case consists of four receiver openings 25 for current electrodes and two receiver openings 26 which are located between the receiver openings 25 for voltage electrodes. In the receiver openings 25, 26 the current and voltage electrodes can be held sealed so that they terminate as flat as possible with the first end 17 or project slightly into the measuring space 4. The function of a conductivity sensor is described in DE 19946315C2. In one advantageous embodiment of the invention the conductivity sensor according to DE 19946315C2 in one receiver opening is suitable for accommodating the housing 1 of the conductivity sensor according to DE 19946315C2 and is also disclosed in combination with it as an invention.

Next to (preferably on the same side of the measuring cell 1) the conductivity receiver 7 there is mechanical coding 15 which with a corresponding pin forms a receiving apparatus or coupling apparatus for coupling of the measuring cell 1 to the process line, and on the measuring cell body 5 there can be several codings 15 which are distributed especially asymmetrically on the measuring cell body 5.

Likewise next to (preferably on the same side of the measuring cell 1) the conductivity receiver 7 there is temperature measurement region 9 in the form of a blind hole 27 which extends almost to the measuring space 4. The blind hole 27 ends in the immediate vicinity of the first end 17 and in the region of the inlet opening 2. Between the blind hole 27 and the first end 17 there is a thin partition 28 through which one measurement tip of a temperature sensor can be inserted so that a reliable measurement and at the same time good sealing relative to the environment are enabled.

On the opposite second end 18 there is a pH measurement receiver 8 for accommodating the pH value measuring means for measuring the pH value of the fluid in the measuring cell 1. The pH measurement receiver 8 comprises a receiver opening 29 whose axial direction is aligned flush with the axial direction of the measuring channel 16. A pH electrode which can be plugged into the receiver opening 29 can thus be plugged sealed against the environment of the measuring cell 1 into the measuring space 4 and measures the pH value of the fluid which is flowing past.

One tip of the pH electrode in the system as claimed in the invention can be advantageously attached in the pH measurement receiver 8 such that it extends at least to under the outlet opening 3, especially at least up to the middle of the outlet opening 3 in the measuring channel 16. The pH electrode can be fixed on the receiver opening 29 sealed.

The measuring cell 1 can be horizontally aligned as claimed in the invention, as is shown in the figures, so that the inlet opening 2 and/or the outlet opening 3 are aligned with the normal. This yields optimum drainage behavior.

The installation space of the measuring cell 1 is further minimized when a beam path runs horizontally for the measurement of the electromagnetic radiation (radiation measurement region 6).

This can be even better optimized by the pH measurement receiver running essentially horizontally, especially at most with an angle of 20° to the horizontal.

REFERENCE NUMBER LIST 1 measuring cell
2 inlet opening
3 outlet opening
4 measuring space
5 measuring cell body
6 radiation measurement region
7 conductivity measurement receiver
8 pH measurement receiver
9 temperature measurement region
10 bend
11 bend
12 connection means
13 connection means
14 reduction
15 coding
16 measuring channel
17 first end
18 second end
19 radiation inlet opening
20 radiation outlet opening
21 window receiver
22 window receiver
23 stops
24 stops
25 receiver openings
26 receiver openings
27 blind hole
28 partition
29 receiver opening

The invention claimed is:

1. A flow through measuring cell for accommodating measuring means for measuring chemical and/or physical properties of a fluid which is flowing through said measuring cell, said measuring cell comprising:
a measuring space located within said measuring cell between an inlet opening for entry of said fluid and an outlet opening for exit of said fluid,
a radiation measurement region in said measuring space, said radiation measurement region being configured to accommodate measurement of an interaction of said fluid with electromagnetic radiation provided to said measuring space from a location outside of said measuring space,
a conductivity measurement receiver configured to accommodate conductivity measuring means for measuring a conductivity of said fluid in said measuring space and/or a pH measurement receiver configured to accommodate pH value measuring means for measuring a pH value of said fluid in said measuring space,
wherein a beam path of said radiation measurement region runs transversely to the measuring space and transversely to said inlet opening and/or said outlet opening,
wherein said inlet opening and said outlet opening run in parallel offset to one another,
wherein said measuring cell is formed as a disposable measuring cell,
wherein said conductivity measurement receiver and/or said pH measurement receiver are located lengthwise to said measuring space and transversely to said inlet opening and/or said outlet opening, and
wherein said conductivity measurement receiver comprises a plurality of receiver openings, each of said receiver openings being configured to accommodate one of a current electrode and a voltage electrode.

2. A flow through measuring cell for accommodating measuring means for measuring chemical and/or physical properties of a fluid which is flowing through said measuring cell, said measuring cell comprising:
a measuring space located within said measuring cell between an inlet opening for entry of said fluid and an outlet opening for exit of said fluid,
a radiation measurement region in said measuring space, said radiation measurement region being configured to accommodate measurement of an interaction of said fluid with electromagnetic radiation provided to said measuring space from a location outside of said measuring space, a conductivity measurement receiver configured to accommodate conductivity measuring means for measuring a conductivity of said fluid in said measuring space and/or a pH measurement receiver configured to accommodate pH value measuring means for measuring a pH value of said fluid in said measuring space, wherein a beam path of said radiation measurement region runs transversely to the measuring space and transversely to said inlet opening and/or said outlet opening, wherein said inlet opening and said outlet opening run in parallel offset to one another, wherein said measuring cell is formed as a disposable measuring cell, wherein said conductivity measurement receiver and/or said pH measurement receiver are located lengthwise to said measuring space and transversely to said inlet opening and/or said outlet opening, wherein said cell includes said conductivity measuring receiver and said pH measurement receiver, wherein said conductivity measurement receiver is positioned adjacent to said inlet opening at a lengthwise end of said measuring space, and wherein said pH measurement receiver is positioned adjacent to said outlet opening at an opposite lengthwise end of said measuring space from said conductivity measurement receiver.

3. A flow through measuring cell for accommodating measuring means for measuring chemical and/or physical properties of a fluid which is flowing through said measuring cell, said measuring cell comprising:

a measuring space located within said measuring cell between an inlet opening for entry of said fluid and an outlet opening for exit of said fluid, a radiation measurement region in said measuring space, said radiation measurement region being configured to accommodate measurement of an interaction of said fluid with electromagnetic radiation provided to said measuring space from a location outside of said measuring space, a conductivity measurement receiver configured to accommodate conductivity measuring means for measuring a conductivity of said fluid in said measuring space and/or a pH measurement receiver configured to accommodate pH value measuring means for measuring a pH value of said fluid in said measuring space, wherein a beam path of said radiation measurement region runs transversely to the measuring space and transversely to said inlet opening and/or said outlet opening, wherein said inlet opening and said outlet opening run in parallel offset to one another, wherein said measuring cell is formed as a disposable measuring cell, wherein said conductivity measurement receiver and/or said pH measurement receiver are located lengthwise to said measuring space and transversely to said inlet opening and/or said outlet opening, wherein said outlet opening is positioned adjacent to a lengthwise end of said measuring space, wherein said pH measurement receiver is positioned on said lengthwise end adjacent to said outlet opening, and wherein said pH measurement receiver is configured to allow a pH electrode to extend through said pH measurement receiver and into said measuring space, said pH electrode extending to a location under a middle of said outlet opening or further into said measuring space.

* * * * *